United States Patent [19]

Hamma et al.

[11] Patent Number: 4,853,378
[45] Date of Patent: Aug. 1, 1989

[54] FLUORINE DERIVATIVES OF VITAMIN $D_3$ AND PROCESS FOR PRODUCING THE SAME

[75] Inventors: Noritaka Hamma, Sakai; Yoshikazu Saito, Nishinomiya; Toshio Nishizawa, Suita; Takashi Katsumata, Toyonaka, all of Japan

[73] Assignee: Sumitomo Chemical Company, Limited, Osaka, Japan

[21] Appl. No.: 108,497

[22] Filed: Oct. 14, 1987

[30] Foreign Application Priority Data

Oct. 20, 1986 [JP] Japan .................. 61-249095

[51] Int. Cl.$^4$ .................. A61K 31/59; C07J 9/00
[52] U.S. Cl. .................. 514/167; 260/397.2
[58] Field of Search .................. 260/397.2; 514/167

[56] References Cited

U.S. PATENT DOCUMENTS

| 4,201,881 | 5/1980 | Deluca | 260/397.2 |
| 4,248,791 | 2/1981 | Deluca et al. | 260/397.2 |
| 4,305,880 | 12/1981 | Deluca et al. | 260/397.2 |
| 4,358,406 | 11/1982 | Deluca et al. | 260/397.2 |
| 4,495,181 | 1/1985 | Norman et al. | 514/167 |
| 4,552,698 | 11/1985 | Deluca | 260/397.2 |

FOREIGN PATENT DOCUMENTS

| 0205025 | 12/1986 | European Pat. Off. |
| 8102298 | 8/1981 | PCT Int'l Appl. |
| 8602527 | 5/1986 | PCT Int'l Appl. |
| 8701705 | 3/1987 | PCT Int'l Appl. |
| 2126234 | 3/1984 | United Kingdom |

OTHER PUBLICATIONS

Chemical Abstracts, vol. 106, No. 19, May 11, 1987, p. 4, Abstract No. 156774y.
Chemical Abstracts, vol. 106, No. 11, Mar. 16, 1987, p. 643, Abstract No. 84955h.
Chemical Abstracts, vol. 102, No. 1, Jan. 7, 1985, p. 549, Abstract No. 6060r.
Chemical Abstracts, vol. 103, No. 15, Oct. 14, 1985, p. 83, Abstract No. 116282t.
Chemical Abstracts, vol. 104, No. 20, May 19, 1986, p. 391, Abstract No. 174464a.
Proceeding of the National Academy of Sciences, vol. 80, Jan. 1983, pp. 201–204, Y. Honma et al.
Pharm. Soc. Japan, 105 th Annual Meeting, Abstracts of Speeches, p. 621, No. 404-1 (1985).

*Primary Examiner*—Douglas W. Robinson
*Assistant Examiner*—Joseph A. Lipovsky
*Attorney, Agent, or Firm*—Stevens, Davis, Miller & Mosher

[57] ABSTRACT

There are disclosed novel derivatives of 26,26,26,27,27,27-hexafluorovitamin $D_3$ having fluorine atom at the 23- and/or 24-position which have an excellent pharmacological activity and a process for production thereof. The novel compounds are represented by the general formula:

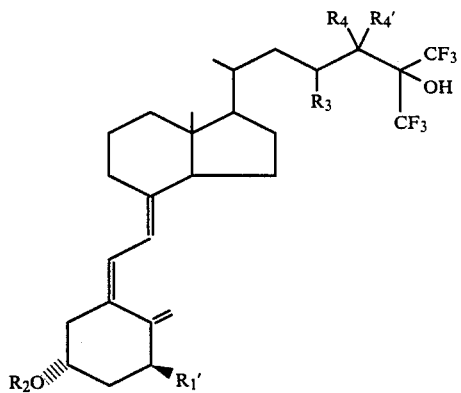

wherein $R_1'$ denotes a hydrogen atom, a hydroxyl group or a protected hydroxyl group, $R_2$ denotes a hydrogen atom or a protecting group for hydroxyl group, $R_3$ denotes a hydrogen atom, a fluorine atom, a hydroxyl group or a protected hydroxyl group and $R_4$ and $R_4'$ each denotes a hydrogen atom, or one of them denotes a hydrogen atom and the other denotes a fluorine atom, hydroxyl group or a protected hydroxyl group or $R_4$ and $R_4'$ are combined to denote an oxo group, with a proviso that at least one of $R_3$, $R_4$ and $R_4'$ denote a fluorine atom. The process for production thereof comprises subjecting to thermal isomerization a compound represented by the general formula:

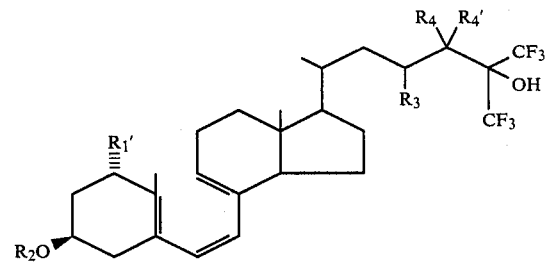

wherein $R_1'$, $R_2$, $R_3$, $R_4$ and $R_4'$ are the same as defined above, to thermal isomerization and optionally further to deprotection reaction.

23 Claims, No Drawings

FLUORINE DERIVATIVES OF VITAMIN $D_3$ AND PROCESS FOR PRODUCING THE SAME

BACKGROUND AND TECHNICAL FIELD OF THE INVENTION

The invention relates to a novel fluorine derivative of vitamin $D_3$. More particularly, it relates to a novel fluorine drivative of vitamine $D_3$ which not only has an excellent pharmacological activity, namely a useful vitamin D-like physiological activity, and is useful as a curative or preventive medicine for various diseases caused by disorders of absorption, transportation or metabolism of calcium, for example bone diseases such as rickets, osteomalacia and osteoporosis, but also has an ability to suppress the proliferation of tumor cells such as myeloleukemia cells and induce the differentiation of these cells into normal cells, is thus useful as an antitumor agent and additionally can be a long-acting medicine. Further, the compound of this invention is useful also as a curative medicine for rheumatism and psoriasis.

PRIOR ART

It is known that $1\alpha,25$-dihydroxyvitamin $D_3$, which is a metabolite of vitamin $D_3$ in a living body and is known as the active-form of vitamin $D_3$, and its artificial homologues, $1\alpha$-hydroxyvitamin $D_3$, $1\alpha,24$-dihydroxyvitamin $D_3$ and the like, exhibit an action of stimulating the absorption of calcium from the intestine and are effective as curatives for bone diseases and the like. Further, there has been found recently in vitamin $D_3$ and its analogous compounds a differentiation-inducing action to restore cancerated cells into normal cells. (Hirobumi Tanaka et al., The Journal of Japanese Biochem. Soc., 55, 1323 (1983)). Actually, some of these compounds have been found to have an antitumor activity (Y. Honma et al., Proc. Natl. Acad. Sci., USA, 80, 201 (1983)) and are attracting attention. However, the results obtained so far are still unsatisfactory.

On the other hand, among the derivatives of vitamin $D_3$ fluorinated at the 26- and the 27-position, 26,26,26,27,27,27-hexafluoro-25-hydroxyvitamin $D_3$ (U.S. Pat. No. 4,248,791) and 26,26,26,27,27,27-hexafluoro-$\alpha a,25$-dihydroxyvitamin $D_3$ (Japanese National Publication (Kohyo) No. 501,176/83) are known to have a high, vitamin D-like physiological activity, and their effectiveness as an antitumor agent is disclosed in Japanese Patent Application Kokai (Laid-open) No. 7,215/86.

Further, a method for preparing 26,26,26,27,27,27-hexafluoro-25-hydroxy-24-oxovitamin $D_3$ is disclosed in Abstracts of lectures, 105-th Anual Meeting of Pharmaceutical Society of Japan, March, 1985).

SUMMARY OF THE INVENTION

The object of this invention is to provide a 26,26,26,27,27,27-hexafluorovitamin $D_3$ derivative having fluorine atom at the 23- and/or the 24-position which is a novel compound and has an excellent pharmacological activity.

DETAILED DESCRIPTION OF THE INVENTION

The fluorine-containing vitamin $D_3$ derivative provided according to this invention is represented by the general formula [1]

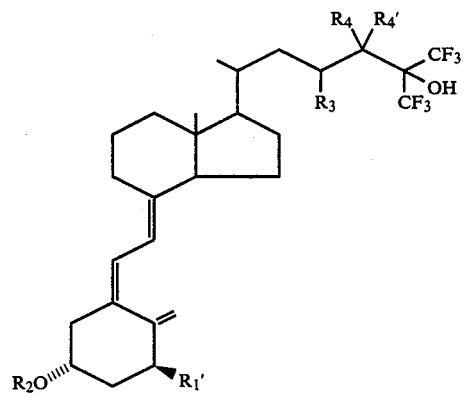

wherein $R_1'$ denotes a hydrogen atom, a hydroxyl group or a protected hydroxyl group, $R_2$ denotes a hydrogen atom or a protecting group for hydroxyl group, $R_3$ denotes a hydrogen atom, a fluorine atom, a hydroxyl group or a protected hydroxyl group and $R_4$ and $R_4'$ each denotes a hydrogen atom, or one of them denotes a hydrogen atom and the other denotes a fluorine atom, a hydroxyl group or a protected hydroxyl group, or $R_4$ and $R_4'$ are combined to denote an oxo group, with a proviso that at least one of $R_3$, $R_4$ and $R_4'$ denotes a fluorine atom. When $R_3$ or $R_4$ or $R_4'$ in the above general formula [1] is a fluorine atom, a hydroxyl group or a protected hydroxyl group, there exists diastereomers attributable to the asymmetric carbon atoms at the 23- and/or the 24-position. This invention includes all of these diastereomers.

Compounds obtained by eliminating all of the protecting groups for the hydroxyl group from the compound of the general formula [1], namely compounds represented by the general formula [1']

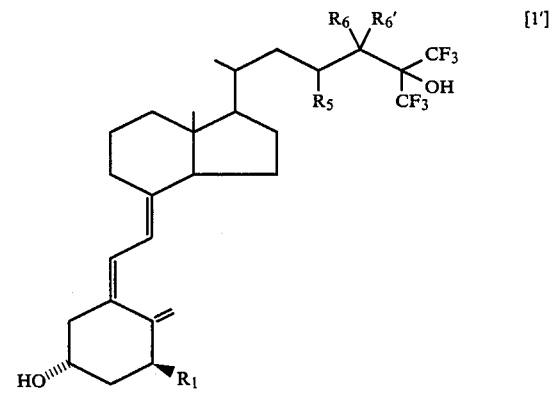

wherein $R_1$ denotes a hydrogen atom or a hydroxyl group, $R_5$ denotes a hydrogen atom, a fluorine atom or a hydroxyl group and $R_6$ and $R_6'$ each denotes a hydrogen atom, or one of them denotes a hydrogen atom and the other denotes a fluorine atom or a hydroxyl group, or $R_6$ and $R_6'$ are combined to denote an oxo group, with a proviso that at least one of $R_5$, $R_6$ and $R_6'$ denotes a fluorine atom, exhibit a vitamin D-like action such as bone formation and is hence useful as a curative or preventive medium for bone diseases; further they exhibit a cell differentiation-inducing action and are hence useful as a cell-differentiation inducing agent or an antitumor agent, and are also useful as an antirheumatic agent for the treatment of cutaneous diseases such as psoriasis.

Further, compounds wherein, in the above-mentioned formula [1], $R_2$ is a protecting group for the hydroxyl group; or $R_1'$ or, $R_3$ or $R_3'$ or $R_4$ or $R_4'$ is a protected hydroxyl group, are useful as an intermediate for producing the compound represented by the general formula [1'] mentioned above.

The compound of the formula [1] of this invention can be prepared by various methods known to the art as the method of preparing vitamin $D_3$ and its analogues. For example, it can be prepared easily and yet advantageously by the method shown by the following reaction scheme.

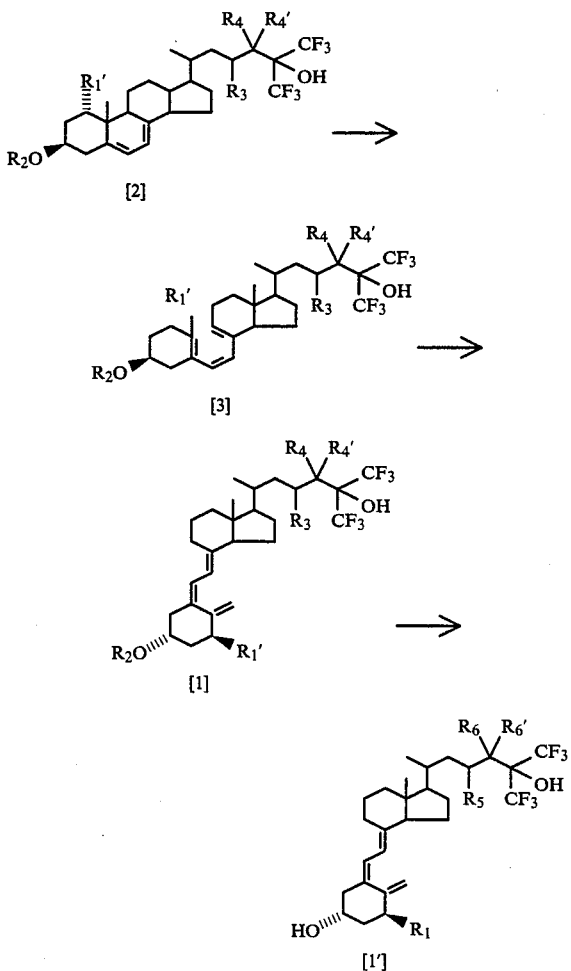

In the above-shown reaction scheme, $R_1$, $R_1'$, $R_2$, $R_3$, $R_4$, $R_4'$, $R_5$, $R_6$ and $R_6'$ have the same meaning as mentioned before. As a protecting group for a hydroxyl group, there can be used a conventional protecting group which is generally used in the art as a protecting group for the hydroxyl group and which can be easily eliminated by conventional means such as a reation with an acid or a base, or reduction. As examples of the protecting groups included in this invention, mention may be made of acyle groups such as alkanoyl groups and aromatic acyle groups; ethereal protecting groups, aralkyl groups, lower alkylsilyl groups, and lower alkoxycarbonyl groups. As more specific examples, there may be mentioned: for alkanoyl groups, lower alkanoyl groups of 2 to 5 carbon atoms such as acetyl, propionyl and pivaloyl; for aromatic acyl groups, an optionally substituted benzoyl group such as benzoyl and p-chlorobenzoyl; for ethereal protective groups, methoxymethyl, 2-methoxyethyl, and 2-tetrahydropyranyl; for aralkyl groups, an optionally substituted benzyl group such as benzyl and p-nitrobenzyl; for lower alkylsilyl groups, trialkylsilyl groups having alkyl groups of 1 to 4 carbon atoms such as trimethylsilyl and dimethyl-t-butylsilyl; and for lower alkoxycarbonyl groups, alkoxycarbonyl groups whose alkoxy moiety has 1 to 4 carbon atoms, such as methoxycarbonyl and ethoxycarbonyl. Among these protecting groups, acyl groups such as acetyl and benzoyl are advantageously used.

Now, procedures for executing the respective reaction steps of the reaction scheme shown above will be described in detail below.

The step for the compound [3] is carried out by a method known per se, namely by irradiating the compound [2] with ultraviolet light. The step of ultraviolet irradiation is carried out by irradiating a compound represented by the general formula [2] with ultraviolet light in a suitable inert solvent, for example, organic solvents such as benzene, toluene, n-hexane, methanol, ethanol, diethyl ether and acetonitrile or the mixture thereof and in an atmosphere of inert gas such as nitrogen and argon. The source of ultraviolet light may be those conventionally used, including, for example, a mercury lamp as an easily available one. A filter may be used together according to necessity. An irradiation temperature of $-10°$ to $40°$ C., preferably $-10°$ to $20°$ C., give good results. Although the irradiation time varies depending on the kind of ultraviolet source, the concentration of the starting compound of the formula [2] and the kind of solvent, it is usually several to several tens of minutes. Although the compound of the formula [3] formed by the ultraviolet irradiation may be isolated by simple means such as chromatography, it may also be possible to carry out thermal isomerization by heating without isolating the compound, thus to follow the reaction scheme continually up to the step for the compound [1].

The reaction step for the compound [1] is also carried out by a method known per se. Thus, it is conducted by heating the compound [3] in a suitable inert solvent at 20° to 120° C., preferably 50° to 100° C., for 2 to 5 hours. The reaction is preferably carried out in an inert gas such as nitrogen or argon. The isolation of the compound [1] from the reaction mixture is effected, after the solvent has been distilled off, by simple means such as chromatography.

As well known, the above photo-reaction and thermal isomerization reaction proceed reversibly by light energy and thermal energy. Therefore, usually the starting compound [2] remains in the reaction liquid after completion of the photo-reaction and this compound [2] is isolated from product [3] and/or product [4] after the irradiation of ultraviolet light or after the subsequent thermal isomerization reaction by chromatography and the like. The thus recovered compound [2] can be re-used to increase yields.

When the compound of the formula [1] thus obtained has the protecting group, it is subjected to a deprotection reaction to obtain the final objective compound of the formula [1'] of this invention. The deprotection reaction may be effected by a method known per se adopted depending on the kind of protecting group mentioned above.

Thus, the compound of the formula [1] of this invention is obtained.

The compound of the formula [2] used as the starting material in the above-mentioned reaction is also a novel compound. Although the compound may be prepared by various methods, it is advantageously obtained, for example, by using the following method found by the present inventors.

First, a compound of the formula [2] wherein $R_3$ is a hydrogen atom, namely a compound represented by the general formula [2-a]

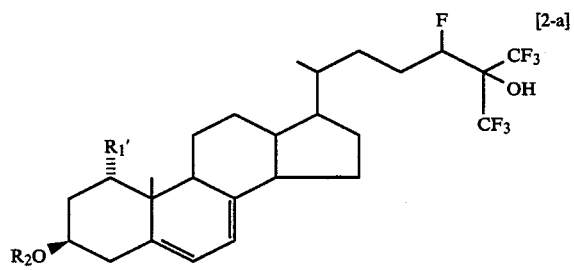

wherein $R_1'$ and $R_2$ are defined above, can be easily obtained by the method shown by the following reaction scheme.

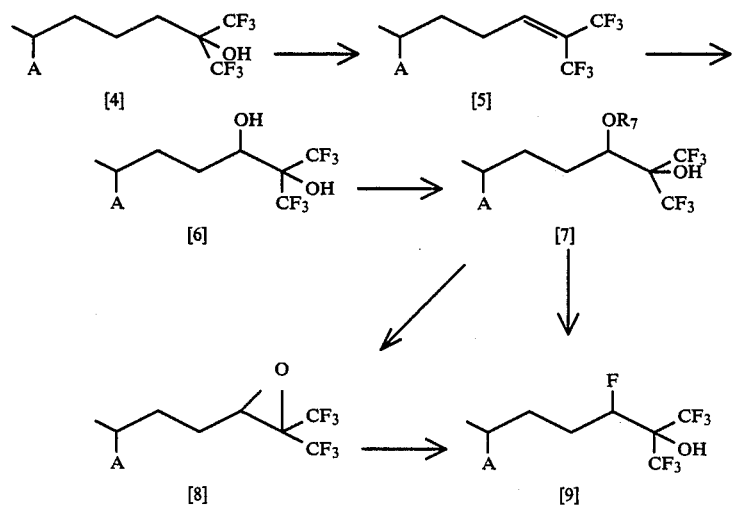

In the above reaction scheme, $R_7$ denotes an alkanesulfonyl group or an arenesulfonyl group and A denotes a steroid residue represented by the general formula [10]:

[10]

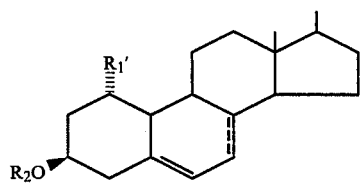

wherein $R_1'$ and $R_2$ are as defined above and the dotted line . . . between the carbon atoms of the 7- and the 8-position signifies the optional presence of a bond.

First, a fluorine derivative of 25-hydroxycholesterol represented by the general formula [4] is treated with a dehydrating agent to give a 24-dehydro compound represented by the general formula [5]. The dehydrating agent used herein is an agent generally used for halogenation of the hydroxyl group, such as thionyl chloride, phosphorus trichloride, phosphorus tribromide, methanesulfonyl chloride, acetyl chloride, and tri-substituted phosphine-carbon tetrahalide. Particularly, tri-substituted phosphine-carbon tetrahalide systems, such as triphenylphosphine-carbon tetrachloride and trioctylphosphine-carbon tetrachloride, give good results. As an example of procedures for executing the present invention, the dehydration of the compound of the formula [4] by means of triphenylphosphine-carbon tetrachloride will be described in detail below. First, triphenylphosphine and carbon tetrachloride are added to the compound of the formula [4] and the mixture is allowed to react at from room temperature to about 100° C. Although a solvent is not necessarily needed in the reaction, an inert organic solvent may also be used. As to the amount of triphenylphosphine and carbon tetrachloride, good results are obtained when they are used respectively in an equimolar amount or more, preferably 1 to 5 molar amount, relative to the starting compound of the formula [4]. The isolation of the objective product of the formula [5] from the reaction mixture can be effected by conventional means such as column chromatography or recrystallization. Thus, the compound of the formula [5] is obtained from the compound of the formula [4] in a high yield. The method of preparation of the starting compound of the formula [4] used herein is disclosed in Japanese National Publication (Kohyo) Nos. 501,176/83 and 500,864/84 and J. Chem. Soc., Chem. Commun., 459 (1980).

Although various methods are conceivable to prepare the compound of the formula [6] from the compound of the formula [5] thus obtained, the following method found by the present inventors is simple and advantageous.

That is, the compound of the formula [5] is dissolved or suspended in a suitable inert solvent such as acetone, methyl ethyl ketone, methylene chloride, chloroform, benzene or toluene, and then a permanganate, such as sodium permanganate or potassium permanganate, is added thereto to effect reaction. In this case, the intended 24-hydroxy compound can be selectively prepared by carrying out the reaction under alkaline conditions by adding an inorganic alkali such as sodium hydroxide, potassium hydroxide, sodium carbonate or potassium carbonate. The amount of the permanganate is about 0.5 to 3 molar amount, preferably about 1 molar amount, relative to the starting compound of the formula [5] to obtain good results. The reaction temperature is about −80° to 50° C.; usually room temperature or below is preferable. The isolation of the intended compound of the formula [6] from the reaction mixture is usually conducted by extracting it, optionally after removing the manganese dioxide formed by filtration, and then treating it by conventional means such as silica gel column chromatography. Thus, the 24-hydroxy compound is obtained.

The 24-oxo derivative represented by the general formula [11] is obtained by carrying out the above reaction with addition of an acid such as formic acid, acetic acid, propionic acid or benzoic acid in place of the inorganic alkali used in the above reaction and then treating the reaction product in the same manner as mentioned for preparation of said 24-hydroxy compound [6].

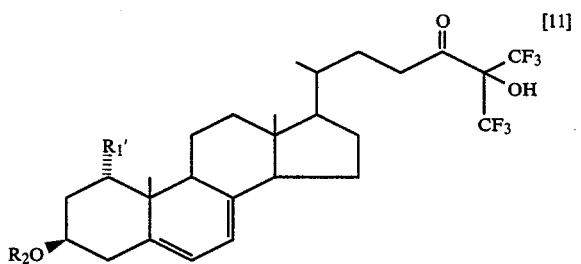

wherein $R_1'$ and $R_2$ are as defined above. The 24-hydroxy derivative represented by the general formula [6] can also be prepared by reducing said compound [11] with a reducing agent such as sodium borohydride.

In this reaction, two kinds of diastereomers are formed which result from the presence of the asymmetric carbon atom of the 24-position. These two kinds of isomers can be separated, if desired, by usual methods of separation and purification, such as column chromatography and recrystallization at each step until preparation of compound [2-a].

The step for compound [7] can be carried out by a method known per se. For example, compound [7] can be easily prepared by reacting compound [6] with an alkanesulfonyl halide such as methanesulfonyl chloride or an arenesulfonyl halide such as benzenesulfonyl chloride or p-toluenesulfonyl chloride in the presence of a tertiary amine base such as pyridine or triethylamine. Reaction temperature of −20° C. to 50° C., preferably 0° C. to room temperature gives good results.

Steps for conversion of thus obtained compound [7] to 24-fluoro compound [9] are carried out, for example, by the following method.

First, compound [7] dissolved or not dissolved in an inert solvent such as benzene, toluene, diethyl ether, tetrahydrofuran or N,N-dimethylformamide is treated with a tertiary amine such as triethylamine or tri-n-butylamine or compound [7] is reacted in the two-layer system of a hydrophobic solvent such as benzene, toluene, n-hexane or chloroform and an aqueous solution of an alkali such as sodium hydroxide or potassium hydroxide in the presence of a phase transfer catalyst such as tetra-n-butylammonium hydroxide or benzyl-tetraethylammonium chloride, thereby to obtain the corresponding epoxy derivative [8] in a high yield. Reaction temperature of this epoxidation of from 0° C. to boiling point of the solvent gives good results, but normally room temperature suffices. Isolation of the resulting compound [8] is carried out by an easy method such as extraction, recrystallization or chromatography.

Compound [9] is easily obtained in a high yield by reacting thus obtained compound [8] with a fluorinating agent in an inert solvent such as benzene, toluene, tetrahydrofuran or dimethylformamide. As the fluorinating agent, thereby may be used salts composed of fluorine ion ($F^-$). As typical examples of the salts, mention may be made of fluorinated inorganic salts such as sodium fluoride, potassium fluoride and cesium fluoride and fluorinated quaternary ammonium salts such as tetra-n-butylammonium fluoride. This fluorination reaction rapidly proceeds by adding at least one mol of a fluoride to compound [8] in said inert solvent at −20° C. to 100° C., preferably 0° C. to 50° C. Isolation of product [9] from the reaction mixture is effected by ordinary methods such as extraction, recrystallization and chromatography. It is also possible to produce compound [9] directly from compound [7]. That is, compound [9] can be obtained easily and in a high yield by treating compound [7] with said fluorides.

The configuration of the 24-position of thus obtained 24-F compound [9] has the same configuration as of the used 24-hydroxy compound [6]. That is, compound [9] wherein the 24-position has R-configuration and compound [9] wherein the 24-position has S-configuration are obtained from compound [6] wherein the 24-position has R-configuration and compound [6] wherein the 24-position has S-configuration, respectively. This configuration is maintained until the objective compound [1'].

When no bond is present between the carbon atoms of the 7- and the 8-positions of steroid skeleton in the compound of the formula [9] thus obtained, a bond can be formed by a method generally used in the art, thereby to convert the compound into a 5,7-diene derivative of the formula [2-a]. Thus, a compound of the formula [2-a], which is included in the compound of the formula [2], can be easily obtained by subjecting a compound of the formula [9] having no bond between the carbon atoms of the 7- and 8-position to halogenation at the 7-position with a halogenating agent such as N-bromosuccinic imide or 1,3-dibromohydantoin and then the dehydrohalogenation with a base such as 2,4,6-collidine or tetra-n-butylammonium fluoride.

Next, a compound of the formula [2] wherein $R_3$ is a fluorine atom is represented by the general formula [2-b]

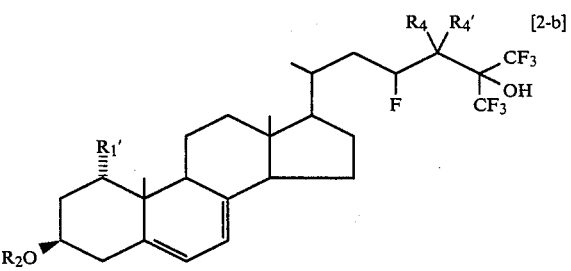

wherein $R_1'$, $R_2$, $R_4$ and $R_4'$ are as defined above and this compound can be prepared, for example, by the method shown in the following reaction scheme.

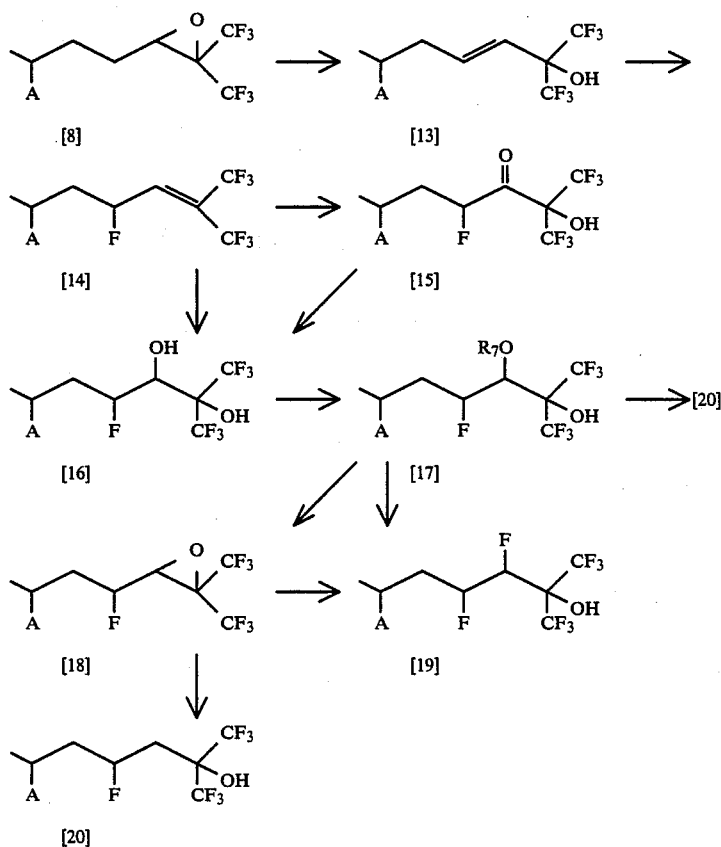

In the above reaction scheme, A and $R_7$ are as defined above. Compounds [15], [16], [19] and [20] produced in the above reaction scheme are all included in the compound of the general formula [2-b].

First, the step for compound [13] can be performed by the method known per se. That is, compound [13] can be obtained almost quantitatively by dissolving the epoxy compound [8] obtained by the above mentioned method in a suitable inert solvent such as benzene, toluene, diethyl ether, tetrahydrofuran or dimethylformamide and treating it with a base such as potassium-t-butoxide or lithium diisopropylamide at a temperature of preferably −20° C. to 50° C.

The step for compound [14] is carried out by reacting the compound [13] with an agent generally used for fluorination of hydroxyl group such as sulfur tetrafluoride ($SF_4$) or diethylaminosulfur trifluoride in an inert solvent such as benzene, toluene, diethyl ether, tetrahydrofuran, dichloromethane or chloroform. A reaction temperature of −80° C. to 50° C., preferably −60° C. to 0° C. gives good results.

The step for compound [15] is performed in substantially the same manner as explained for the production of compound [11] from compound [5], namely, the reacting compound [14] with a permanganate in the presence of an acid and thus compound [15] can be obtained in a high yield.

Reduction from 24-oxo compound [15] to 24-hydroxy compound [16] is carried out by the method known per se, namely, by treating compound [15] with a reducing agent generally used for reduction of ketones to alcohols such as lithium aluminum hydride, sodium borohydride or diisobutylaluminum hydride in an inert solvent. Compound [16] can also be produced by the same method as the oxidation from compound [5] to compound [6] mentioned above, namely, by reacting compound [14] with a permanganate in the presence of an alkali.

The step from compound [16] to compound [19] through sulfonate compound [17] and epoxy compound [18] can be effected in the same manner as explained for the step from compound [6] to compound [9] through compounds [7] and [8]. Further, compound [19] can be directly obtained by reacting compound [17] with the fluoride referred to in the production of compound [9].

The step from epoxy compound [18] to compound [20] is performed by the method known per se, namely, by treating epoxy compound [18] with a reducing agent commonly used for reduction of epoxy group such as lithium aluminum hydride and thus compound [20] can be obtained in a high yield. Compound [20] can also be produced by treating compound [17] in the same manner as the reduction of compound [18].

When no bond is present between the carbon atoms of the 7- and 8-positions of steroid skeleton in thus obtained compounds [15], [16], [19] and [20], these compounds can be converted into corresponding 5,7-diene derivatives [2-b] by subjecting them to halogenation at the 7-position and then dehydrohalogenation as in the case of compound [9].

A compound of the general formula [2] wherein $R_3$ is a hydroxyl group or a protected hydroxyl group, namely, a compound represented by the general formula [2-c]

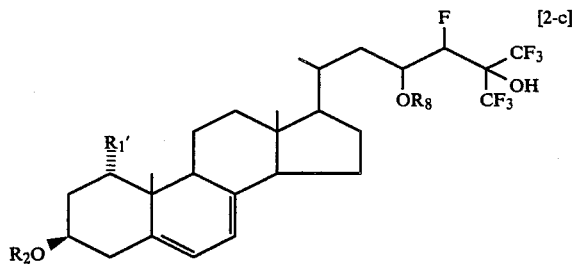

wherein $R_1'$ and $R_2$ are as defined above and $R_8$ denotes a hydrogen atom or a protecting group for hydroxyl group, can be produced by the method shown by the following reaction scheme.

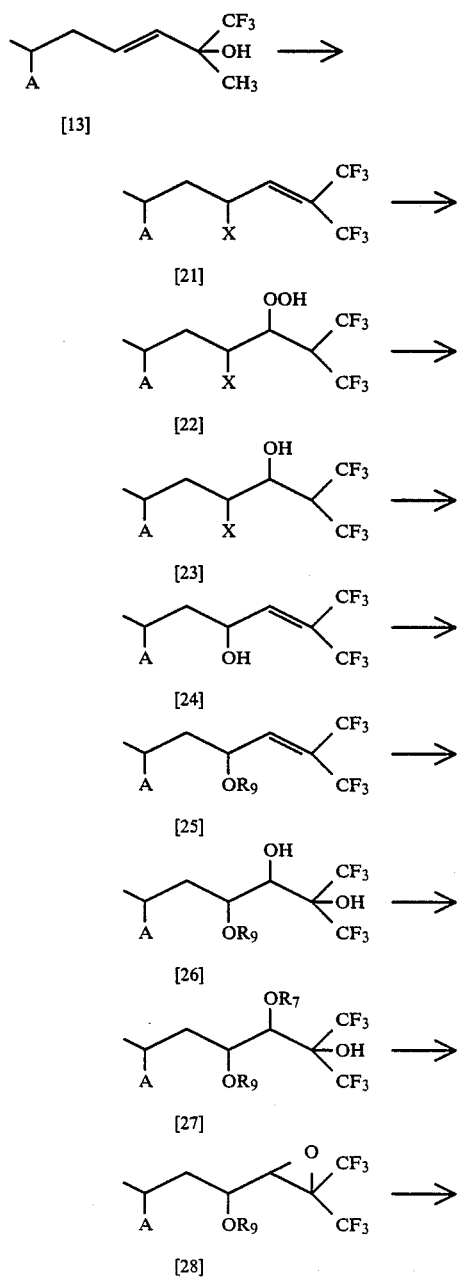

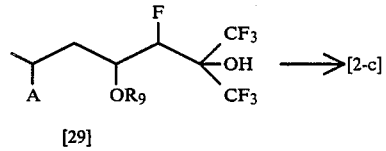

In the above reaction scheme, A and $R_7$ are as defined above, $R_9$ denotes a protecting group for hydroxyl group and X denotes a chlorine atom or a bromine atom. As the protecting group for hydroxyl group, those exemplified above are used.

A series of reactions mentioned above will be explained in further detail. First, transformation from compound [13] to compound [21] can be preformed by reacting compound [13] with a halogenating agent generally used for chlorination or bromination of hydroxyl group. Thus, compound [21] can be obtained easily and high yields. The halogenating agent and the reaction method used here can be the same as those used in the dehydration reaction of compound [4] to compound [5] mentioned before. Compound [21] obtained in this method is usually a mixture of two diastereomers which result from the presence of the asymmetric carbon atom of the 23-position. These diastereomers can be separated, if desired, by usual methods such as recrystallization and column chromatography.

The step for compound [22] is performed by dissolving compound [21] in a suitable inert solvent and reacting therewith hydrogen peroxide in the presence of a base. Inorganic alkalis such as sodium hydroxide, potassium hydroxide and potassium carbonate can be used satisfactorily as the bases and a catalytic amount of 0.01–0.5 molar amount for compound [21] can give good results. Hydrogen peroxide is used in an excessive amount of 5–100 moles for 1 mol of compound [21]. A reaction temperature of 0° to 50° C., preferably about room temperature gives good results.

The step for the compound [23] is easily performed by treating the compound [22] by a reduction method generally used for the reduction of hydroperoxides. In the case of the compound of this invention, the most simple method is to reduce the compound [22] with an alkali metal iodide such as potassium iodide or sodium iodide.

The step for the compound [24] is performed by treating the compound [23] with a base, Though both organic and inorganic bases may be used, quaternary ammonium salts give particularly a good result. Thus, a good result is obtained by a method comprising dissolving or suspending the compound [23] in a solvent immiscible with water, such as n-hexane, benzene, toluene, xylene, 1,2-dichloroethane and chloroform, then adding an aqueous solution of caustic alkali, such as sodium hydroxide and potassium hydroxide, and further a quaternary ammonium salt thereto, and allowing the resulting mixture to react in a two-layer system. The quaternary ammonium salts used in this invention include those compounds which are generally used as a phase transfer catalyst. As specific examples thereof, mention may be made of quaternary ammonium halides such as tetra-n-butylammonium chloride and benzyltriethylammonium chloride, and quaternary ammonium hydroxides such as tetra-n-butylammonium hydroxide. These phase transfer catalysts give a good result at 0.01 to 0.5 molar amount thereof relative to the compound [23]. The reaction is carried out at room temperature to 150° C., but usually at the reflux temperature of the solvent used. The configuration of the 23-position undergoes inversion in the reaction, whereby the compound [24], wherein the 23-position has S-configuration, is obtained from the compound [21] wherein the 23-position has R-configuration.

The step for compound [25] can be easily performed by subjecting compound [24] to generally employed protecting reaction depending on the kind of protecting group $R_9$.

The step from compound [25] to compound [29] through compounds [26], [27] and [28] can be performed by the method explained for the steps from compound [5] to compound [9] through compounds [6], [7] and [8] and thus, compound [29] can be obtained in a high yield.

When no bond is present between the carbon atoms of the 7- and 8-positions of steroid skeleton in the thus obtained compound [29], this compound can be easily converted to a corresponding 5,7-diene derivative by subjecting it to halogenation at the 7-position and then dehydrohalogenation as in the case of compound [9]. If necessary, this diene derivative can be converted to a compound represented by the general formula [2-c] by elimination of the protecting group represented by $R_9$.

As explained in detail hereinabove, compound [2] having a fluorine atom at the 24-position can be produced by utilizing the following reactions, namely, by reacting with a fluorinating agent a compound of the general formula [30]

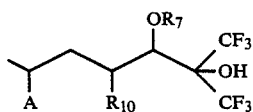
[30]

wherein A and $R_7$ are as defined above and $R_{10}$ denotes a hydrogen atom, a fluorine atom or a protected hydroxyl group, or an epoxy derivative of the formula [31]

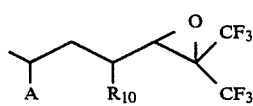
[31]

wherein A and $R_{10}$ are as defined above and then, if necessary, eliminating the protecting group for hydroxyl group, thereby to obtain a derivative substituted with fluorine at the 24-position which is represented by the general formula [32] and is included in compound [2]

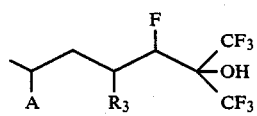
[32]

wherein A and $R_3$ are as defined above.

Although sometimes all or part of the protecting groups for the hydroxyl group will detach themselves depending on the kinds of the protecting groups and the reagents, reaction conditions etc. used in each step of teh preparation process mentioned above, it is needless to say that in such cases the protecting group can be reintroduced by subjecting the product to reprotection reaction as occasion demands.

Thus, the compound [2] is obtained and further the compound [1] is prepared. Not only the objective compound [1] of this invention but also every intermediate compound formed in each of the above-mentioned reaction steps is a novel compound not described in the literature.

The compound [1'] thus obtained is administered parenterally, for example by intramuscular or intravenous injection, or orally, or as suppositories, or further by application to the skin as external remedies. The dosage can be appropriately selected depending on the method of administration within the range from 0.002 to about 100 μg, preferably 0.01 to 20 μg per one day for adult. In oral administration, for example, the dosage can be determined in the range from 0.01 to 50 μg, preferably 0.02 to 10 μg.

The pharmaceutical preparations of the compound [1] are prepared in combination thereof with pharmaceutically acceptable carriers known to the art, which carriers may be either solid or liquid. Specific examples of carriers to be used include maize starch, olive oil, sesame oil, and a triglyciride of medium chain fatty acid generally called MCT. The dosage forms used include, for example, tablets, capsules, liquids, powders, granules and creams.

Now, the pharmacological effect of the compound of this invention will be described below by way of experimental data.

The activity in increasing of serum calcium of the compound of this invention in normal rats.

Experimental method

A 95% ethanol solution of the compound or 95% ethanol alone (for control group) was aminidtered intrajugularly to Wistar male rats of 6 weeks old. Blood was collected from tail artery after 24 hours and 48 hours and concentration of calcium in serum was determined by the OCPC (orthocresolphthalein complexon) method.

Results of experiments

The results of experiments are shown in Table 1.

TABLE 1

| | Serum calcium increasing response in normal rats | | |
|---|---|---|---|
| | Dose (p mol/ 100 g body wt.) | Concentration of serum calcium (mg/100 ml) | |
| Compound | | 24 hours after administration | 48 hours after administration |
| Control | — | 10.5 ± 0.17 | 9.5 ± 0.32 |
| 1a, 25-dihydroxy-vitamin $D_3$ | 130 | 11.2 ± 0.20* | 10.2 ± 0.79 |
| Compd. (10a) | 130 | 12.6 ± 0.28** | 12.8 ± 0.39** |
| of this (20a) | 130 | 12.8 ± 0.42** | 13.6 ± 0.76** |
| inven- (21a) | 130 | 13.1 ± 0.41** | 13.2 ± 0.46** |
| tion (23a) | 130 | 11.7 ± 0.33** | 11.6 ± 0.86** |
| (23b) | 130 | 13.4 ± 0.33** | 12.7 ± 0.39** | |

Mean ± SD (n = 5 − 6)
*, **P < 0.05, P < 0.01 against control

Differentiation of human premyeloblast leukemia cells (HL-60) into macrophages induced by the compound of this invention

Experimental method

Proliferation-suppression rate

An HL-60 cell fluid adjusted to a concentration of $5 \times 10^4$ cells/ml was incorporated with each of the agents to be tested and cultivated in a carbon dioxide incubator at 37° C. for 4 days. After the cultivation, the number of cells was measured by means of a Coulter counter. The percentage of the number thus measured relative to the number of cells in an untreated group was calculated, from which the proliferation-suppression rate was obtained.

NBT reduction

HL-60 cells were treated with the agent to be tested for 4 days, and then a growth medium (95% RPMI-1640, 5% FCS) and a 0.2% NBT solution containing 200 ng/ml of TPA (12-o-tetradecanoylphorbol-13-acetate) were added thereto in an equal amount, and the resulting mixture was incubated at 37° for 30 minutes. Thereafter, the cells were smeared onto a slide glass, subjected to Giemsa staining, and the coloration of the cells was examined under a microscope. The number of cells containing intracellular blue-black formazan deposits was measured for 200 cells, and the results were expressed in terms of the percentage of NBT reduction-positive cells.

Results of experiments

The results of the experiments are shown in Tables 2 and 3.

TABLE 2

| Compound | | Conc. (ng/ml) | Proliferation-supppression rate (%) | NBT reduction rate (%) |
|---|---|---|---|---|
| Control | | | 0 | 0.5 |
| 1a, 25-dihydroxy-vitamin D$_3$ | | 10 | 72.4 | 56.5 |
| | | 1 | 36.1 | 16.5 |
| | | 0.1 | 6.2 | 1.0 |
| Compound of this invention | (10a) | 10 | 84.8 | 80.0 |
| | | 1 | 72.2 | 61.0 |
| | | 0.1 | 26.3 | 10.0 |
| | (10b) | 10 | 82.8 | 90.0 |
| | | 1 | 72.6 | 67.0 |
| | | 0.1 | 21.8 | 6.0 |

TABLE 3

| Compound | | Conc. ($\times 10^{-10}$M) | Proliferation-suppresssion rate (%) | NBT reduction rate (%) |
|---|---|---|---|---|
| Control | | | 0 | 0 |
| 1a,25-dihydroxy-vitamin D$_3$ | | 100 | 49.5 | 50.0 |
| | | 10 | 19.5 | 3.0 |
| | | 1 | 2.8 | 0 |
| Compound of this invention | (20a) | 10 | 85.7 | 74.0 |
| | | 3 | 50.0 | 21.0 |
| | | 1 | 12.7 | 3.5 |
| | (21a) | 10 | 81.4 | 76.0 |
| | | 3 | 66.5 | 60.5 |
| | | 1 | 28.1 | 18.5 |
| | (23a) | 10 | 61.2 | 67.0 |
| | | 3 | 21.0 | 39.0 |
| | | 1 | 8.0 | 3.5 |
| | (23b) | 10 | 77.2 | 80.0 |
| | | 3 | 54.0 | 37.5 |
| | | 1 | 33.2 | 20.0 |

Preferred Embodiments of the Invention

This invention will be described in more detail below with reference to Examples. In the Examples, Ac denotes the acetyl group, Ms denotes the methanesulfonyl group, and B denotes a steroid residue represented by the general formula

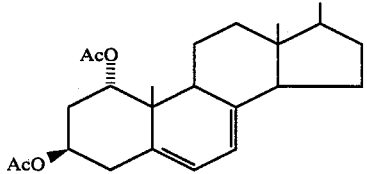

wherein Ac denotes the acetyl group.

Example 1

Preparation of 24(R)-1α,25-dihydroxy-24,26,26,26,27,27,27-heptafluorovitamin D$_3$ (Compound 10a)

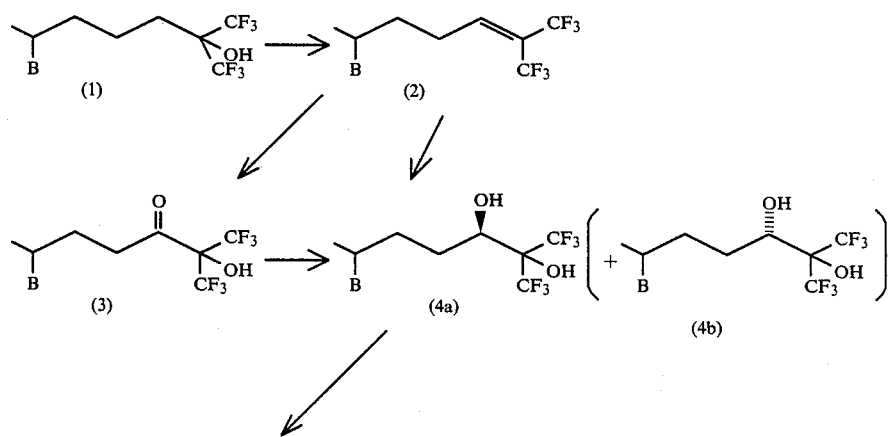

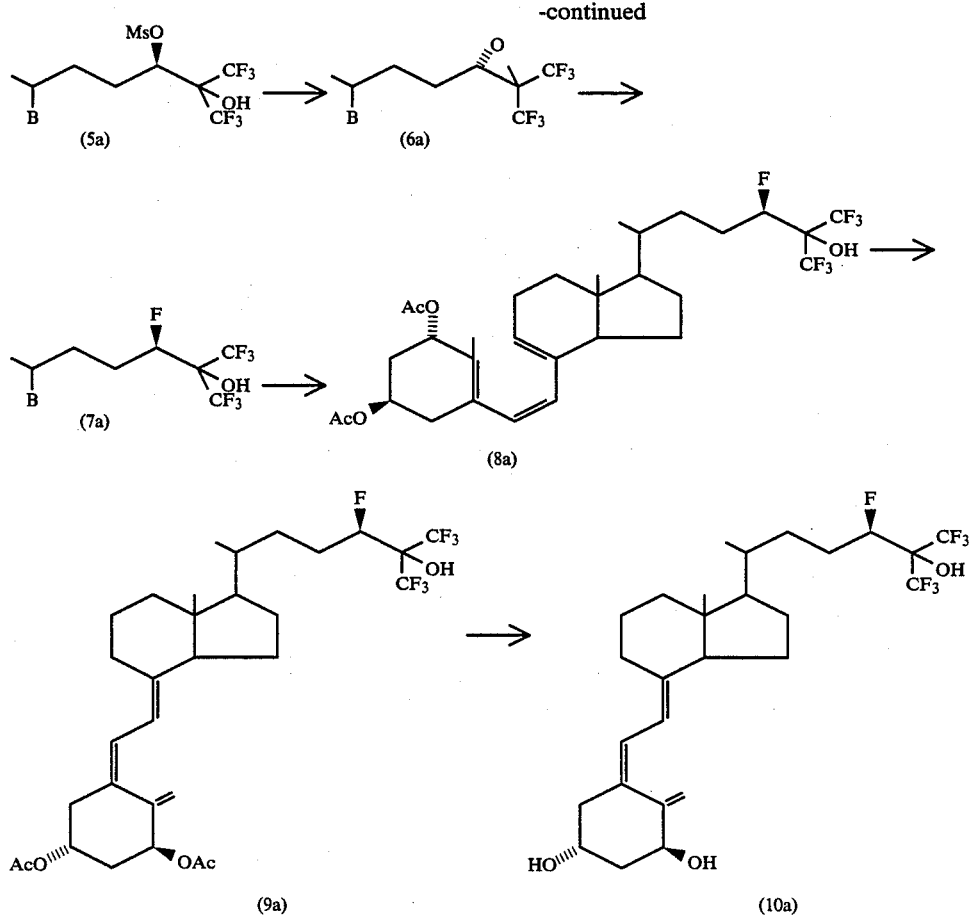

(1) Preparation of compound (2)

A solution of 1.5 g of 1a, 3β-diacetoxy-26,26,26,27,27,27-hexafluoro-25-hydroxycholesta-5,7-diene (1) synthesized by substantially the same method as described in Japanese National Publication (Kohyo) No. 501,176/83, 3.0 g of triphenylphosphine and 3 ml of carbon tetrachloride in 50 ml of 1,2-dichloroethane was heated under reflux in nitrogen atmosphere for 15 minutes. The reaction mixture was cooled down to room temperature, concentrated under reduced pressure, and the residue was subjected to silica gel column chromatography. Fractions eluted with ethyl acetate-n-hexane (1: 10) were collected and recrystallized from methanol to obtain 1.38 g (95% yield) of the intended 5,7,24-triene compound (2).

m.p. 116°–118° C.

IR (Nujol, cm$^{-1}$): 1735, 1670

NMR (CDCl$_3$, δ): 0.62 (3H, s), 0.98 (3H, d, J=6.6 Hz), 1.01 (3H, s), 2.03 (3H, s), 2.09 (3H, s), 5.00 (2H, m), 5.40 (1H, m), 5.68 (1H, m), 6.73 (1H, t, J=8.0 Hz)

UV (EtOH, nm): λmax 271.5, 281, 293

(2) Preparation of compounds (4a) and (4b)

① Method A

One hundred milliliters of acetone and 400 mg of potassium carbonate were added to 487 mg of the compound (2). While the mixture was being maintained at −15° C. in an ice-salt bath, 117 mg of potassium permanganate was added thereto, and the mixture was stirred for 1 hour. The mixture was further stirred at 0° C. for 30 minutes, then solvent was removed therefrom, and 100 ml of ethyl acetate and 100 ml of 1 N hydrochloric acid were added to the residue and stirred. The mixture was filtered to remove manganese dioxide and the filtrate was separated into layers. The organic layer was washed once with 50 ml of a 3% aqueous sodium bicarbonate solution, then twice with 100 ml of water, and extracted with ethyl acetate. The reaction product was subjected to silica gel column chromatography and eluted with n-hexane-ethyl acetate mixture (10:1) to obtain 235 mg (46% yield) of a mixture of the compounds (4a) and (4b)

NMR (CDCl$_3$, δ): 0.62 (3H, s), 0.96 and 0.97 (respectively 1.5H, d, J=6.0 Hz), 1.01 (3H, s), 2.04 (3H, s), 2.08 (3H, s), 3.91 (1H, t, J=12.3 Hz), 4.99 (2H, m), 5.39 (1H, d, J=3.0 Hz), 5.68 (1H, d, J=3.0 Hz)

This product showed two peaks of the same area ratio at 5.1 minutes and 5.8 minutes in high-performance liquid chromatography (referred to as "HPLC" hereinafter) (column: Zorbax BP SIL® 4.6 mmØ×15 cm, carrier: ethyl acetate-n-hexane 1:6, flow rate: 2.5 ml/minute). A 230 mg portion of this product was subjected again to silica gel column chromatography and eluted with n-hexane-ethyl acetate (8:1). The eluted product was separated into an isomer (4b) of low polarity and an isomer (4a) of high polarity. Thus, 63 mg of the pure isomer (4b) and 49 mg of the pure isomer (4a) were obtained.

Isomer (4b)

NMR (CDCl$_3$, δ): 0.62 (3H, s), 0.97 (3H, d, J=6.3 Hz), 1.01 (3H, s), 2.04 (3H, s), 2.09 (3H, s), 2.65 (1H, m), 3.88 (1H, d-d, J=9.2 Hz, 10.2 Hz), 4.24 (1H, s), 4.99

(1H, m), 5.00 (1H, d, J=4.0 Hz), 5.39 (1H, d-t, J=5.6 Hz, 3.0 Hz), 5.68 (1H, d-d, J=3.3 Hz, 5.6 Hz)

Isomer (4a)

NMR (CDCl$_3$, δ): 0.63 (3H, s), 0.96 (3H, d, J=6.3 Hz), 1.01 (3H, s), 2.04 (3H, s), 2.09 (3H, s), 2.66 (1H, m), 3.94 (1H, d-d, j=8.3 Hz, 10.2 Hz), 4.24 (1H, s), 4.99 (1H, m), 5.00 (1H, d, J=3.6 Hz), 5.39 (1H, d-t, J=5.6 Hz, 3.0 Hz), 5.68 (1H, d-d, J=2.7 Hz, 5.6 Hz)

Thus obtained isomer (4b) was recrystallized from a mixed solvent of ethyl acetate-n-hexane and the resulting columnar crystal was subjected to X-ray crystallographic analysis to confirm that its 24-position was in S-configuration. Therefrom, the isomer (4a) was determined to be in R-configuration.

② Method B

In 150 ml of acetone, 300 mg of compound (2) was dissolved and 0.5 ml of glacial acetic acid was added thereto. While the mixture was being maintained at −15° C. in an ice-salt bath, 80 mg of potassium permanganate was added thereto and the mixture was stirred for 2 hours. The mixture was further stirred at 0° C. for 30 minutes, then 1 ml of methanol was added thereto and heated to room temperature. Then solvent was removed under reduced pressure and 100 ml of ethyl acetate and 100 ml of 1N hydrochloric acid were added thereto, followed by stirring. The mixture was filtered to remove manganese dioxide and the filtrate was separated into layers. The organic layer was washed once with 50 ml of a 3% aqueous sodium bicarbonate solution, once with 50 ml of saturated aqueous sodium chloride solution and then twice with 100 ml of water and extracted with ethyl acetate. The organic layer was concentrated under reduced pressure and the residue was subjected to silica gel column chromatography and eluted with n-hexane-ethyl acetate (5:1) to obtain 233.4 mg (75% yield) of compound (3).

NMR (CDCl$_3$, δ) 0.62 (3H, s), 0.94 (3H, d, J=5.6 Hz), 1.01 (3H, s), 2.04 (3H, s), 2.09 (3H, s) 5.01 (3H, m), 5.41 (1H, m), 5.70 (1H, m)

In 30 ml of tetrahydrofuran, 200 mg of thus obtained compound (3) was dissolved and the solution was cooled to 0° to 5° C., followed by adding 60 mg of sodium borohydride and stirring at the same temperature for 30 minutes. The reaction mixture was extracted with addition of water and ethyl acetate. The organic layer was washed with water and concentrated under reduced pressure to obtain 200 mg (99% yield) of compound (4). This product was a mixture of compounds (4a) and (4b)=53:47 according to HPLC.

(3) Preparation of compound (5a)

In 5 ml of anhydrous pyridine, 46 mg of compound (4a) was dissolved and 0.2 g of methanesulfonyl choride was added to the solution. This was left to stand at 5° C. for 20 hours. Water was added to the reaction mixture and this was extracted with benzene. The organic layer was washed successively with water, 1N HCl and water, dried (over MgSO$_4$) and then concentrated. Thus obtained concerntrated residue was used, as it was, in the subsequent step.

(4) Preparation of compound (6a)

The concentrated residue of the above compound (5a) was dissolved in 5 ml of triethylamine and the solution was allowed to stand at room temperature for 1 hour. The reaction mixture was concentrated and the residue was purified by silica gel column chromatography (eluting solution: ethyl acetate-n-hexane 1:10) to obtain 44.6 mg (94% yield relative to compound (4a)) of compound (6a).

NMR (CDCl$_3$, δ) 0.62 (3H, s), 0.97 (3H, d, J=6.3 Hz), 1.01 (3H, s) 2.04 (3H, s), 2.09 (3H, s), 3.43 (1H, m), 5.0 (2H, m), 5.4 (1H, m), 5.7 (1H, m)

(5) Preparation of compound (7a)

In 10 ml of tetrahydrofuran, 40 mg of thus obtained compound (6a) was dissolved and thereto was added 0.2 g of tetra-n-butylammonium fluoride. The reaction mixture was stirred at room temperature for 30 minutes, then water was added thereto and the mixture was extracted with toluene. The toluene layer was washed with 1N HCl and water and concentrated. The residue was subjected to silica gel column chromatography (eluting solution: ethyl) acetate-n-hexane 1:10) to obtain 30 mg (94% yield) of compound (7a). This product was confirmed to be a pure diastereomer (7a) according to NMR and HPLC.

NMR (CDCl$_3$, δ) 0.63 (3H, s), 0.96 (3H, d, J=6.3 Hz), 1.01 (3H, s), 2.03 (3H, s), 2.09 (3H, s) 4.75 (1H, d-d, J=45.5 Hz, 10.5 Hz), 5.0 (2H, m), 5.4 (1H, m), 5.7 (1H, m)

(6) Preparation of compound (10a)

In a mixed solvent of 280 ml of benzene and 120 ml of n-hexane, 30 mg of compound (7a) was dissolved. The solution was cooled to 0° to 5° C. and irradiated with ultraviolet light by use of a 100 W high pressure mercury lamp under an argon atmosphere for 20 minutes. The reaction mixture was refluxed for 4 hours to carry out thermal isomerization and solvent was distilled off under reduced pressure to obtain a crude product of compound (9a). This crude product was dissolved in 30 ml of a 5% methanolic sodium hydroxide solution and was left to stand in a nitrogen stream at 5° overnight. To the reaction mixture was added 100 ml of 1N HCl, followed by extraction with ethyl acetate. The organic layer was washed with water and concentrated. The residue was purified twice by silica gel column chromatography (eluting solution: ethyl acetate-n-hexane 2:3) to obtain 5.8 mg (22% yield) of the objective compound (10a). This product was confirmed to be a pure diastereomer (10a) according to NMR.

UV (EtOH, nm): λmax 212, 264; λmin 228

NMR (CDCl$_3$, δ) 0.56 (3H, s), 0.96 (3H, d, J=6.2 Hz), 4.23 (1H, m), 4.44 (1H, m), 4.74 (1H, d-d, J=46.2 Hz, 10.9 Hz), 5.01 (1H, m), 5.33 (1H, m), 6.02 (1H, d, J=11.2 Hz), 6.38 (1H, d, J=11.2 Hz)

Example 2

Preparation of 24(S)-1α,25-dihydroxy-24,26,26,26,27,27,27-heptafluorovitamin D$_3$ (compound 10b).

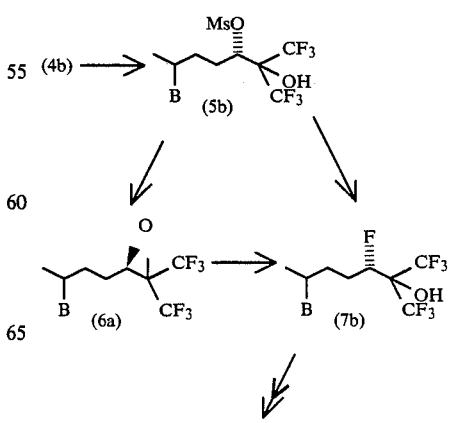

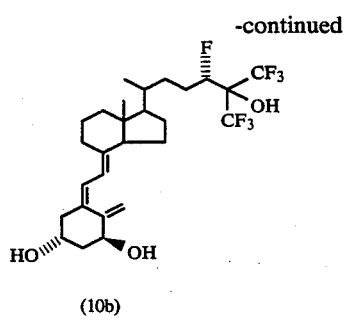

(10b)

(1) Preparation of compound (5b)

A 50 mg portion of the compound (4b) obtained in (2) of Example 1 as treated in the same manner as in preparation of compound (5a) in Example 1 to obtain 55 mg (98% yield) of compound (5b)

(2) Preparation of compound (7b)

① Method A

Forty milligrams of said compound (5b) was treated with triethylamine in the same manner as in preparation of compound (6a) in Example 1 to obtain 33 mg (95% yield) of compound (6b).

NMR (CDCl$_3$, δ) 0.63 (3H, s), 0.96 (3H, d, J=6.6 Hz) 1.01 (3H, s), 2.04 (3H, s), 2.09 (3H, s), 3.41 (1H, m), 5.0 (2H, m), 5.4 (1H, m), 5.7 (1H, m)

Thirty milligrams of thus obtained compound (6b) was treated in the same manner as in preparation of compound (7a) in Example 1 to obtain 28 mg (90% yield) of compound (7b)

NMR (CDCl$_3$, δ) 0.62 (3H, s), 0.97 (3H, d, J=6.6 Hz), 1.01 (3H, s), 2.04 (3H, s), 2.09 (3H, s), 4.70 (1H, d-d, J=45.9 Hz, 10.9 Hz), 5.0 (2H, m), 5.4 (1H, m), 5.7 (1H, m)

② Method B

In 5 ml of 1M tetra-n-butylammonium fluoridetetrahydrofuran solution, 9 mg of compound (5b) was dissolved. The solution was allowed to stand at room temperature for 1 hour and then water was added thereto and this was extracted with toluene. The toluene layer was washed with 1N HCl and water and concentrated. The residue was subjected to silica gel column chromatography (eluting solution: ethyl acetate-n-hexane 1:10) to obtain 7.5 mg (93% yield) of compound (7b). This product showed the same NMR spectrum as that of compound (7b) obtained by the above method A.

(3) Preparation of compound (10b)

Thirty milligrams of compound (7b) was treated in the same manner as in preparation of compound (10a) in Example 1 to obtain 6.5 mg (25% yield) of the objective compound (10b).

UV (EtOH, nm): λmax 212, 264; λmin 228

NMR (CDCl$_3$, δ) 0.56 (3H, s), 0.96 (3H, d, J=6.3 Hz), 4.21 (1H, m), 4.42 (1H, m), 4.70 (1H, d-d, J=45.5 Hz, 10.6 Hz), 5.01 (1H, m), 5.33 (1H, m), 6.02 1H, d, J=11.2 Hz), 6.38 (1H, d, J=11.2 Hz)

Example 3

Preparation of 23(S), 24(S)-1α,25-dihydroxy-23,24,26,26,26,27,27,27-octafluorovitamin D$_3$(compound 20a)

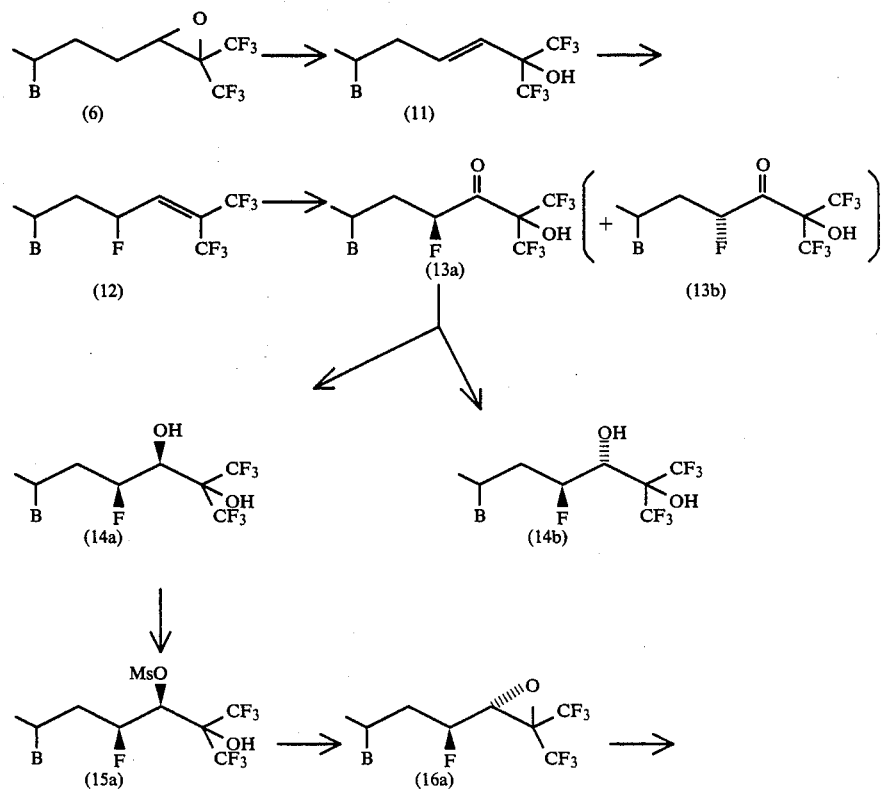

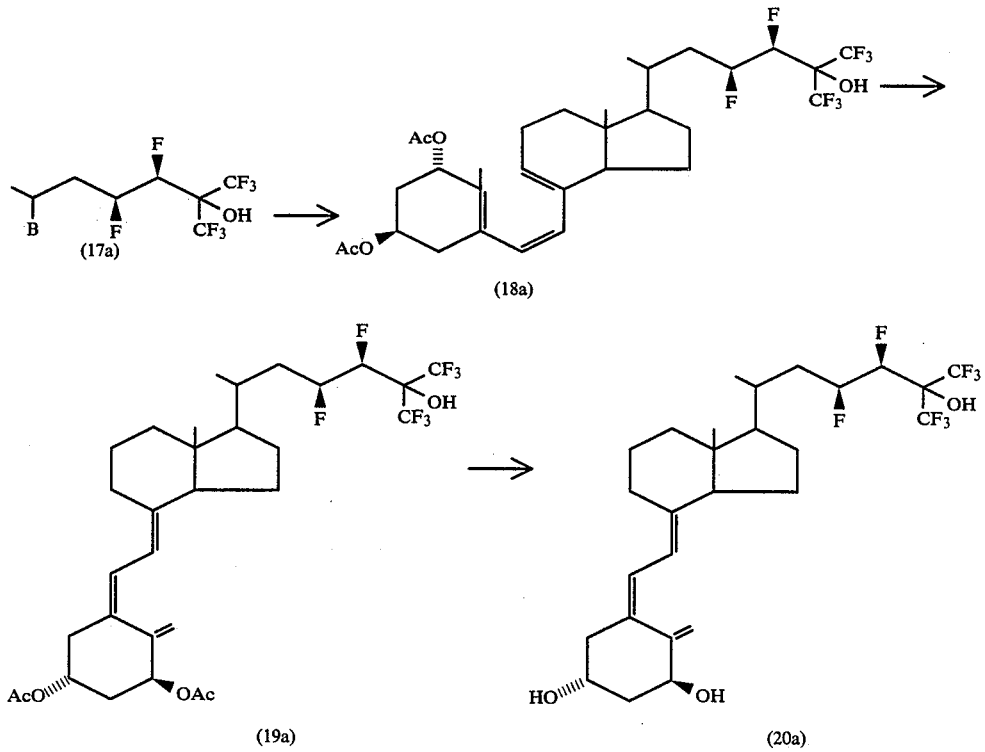

(1) Preparation of compound (11)

To a tetrahydrofuran solution (200 ml) containing 2.1 g of lithium diisopropylamide cooled to −10° C. was added 4.26 g of epoxide (6) prepared by the method of Example 1 and the mixture was stirred at −10° C. to −5° C. for 50 minutes. The reaction mixture was extracted with addition of 50 ml of 1N hydrochloric acid, 500 ml of saturated aqueous sodium chloride solution and 300 ml of ethyl acetate and the organic layer was washed with water and then concentrated. The residue was purified by silica gel column chromatography (eluting solution: ethyl acetate-n-hexane 1:5) to obtain 3.81 g (89.5% yield) of compound (11).

NMR (CDCl$_3$, δ): 0.68 (3H, s), 0.89 (3H, d, J=6.6 Hz), 1.08 (3H, s), 2.03 (3H, s), 2.06 (3H, s), 3.30 (1H, s), 4.9 (1H, m), 5.05 (1H, m), 5.53 (1H, m), 5.57 (1H, d, J=15.8 Hz), 6.27 (1H, m)

(2) Preparation of compound (12)

A mixture of 2.6 g of compound (11) and 50 ml of dichloromethane was cooled to −30° C., followed by adding 0.8 ml of diethylaminosulfur trifluoride (Et$_2$NSF$_3$) in a nitrogen atmosphere. The reaction mixture was stirred at −35° C. to −30° C. for 2 hours, followed by adding water and extraction with dichloromethane. The organic layer was washed with water, dried (over MgSO$_4$) and concentrated under reduced pressure. The residue was purified by silica gel column chromatography to obtain 1.72 g (66% yield) of compound (12). This product was a mixture (2:3) of an isomer where the 23-position had R-configuration and an isomer where the 23-position had S-configuration according to NMR.

NMR (CDCl$_3$, δ) of the compound of 23(R) isomer and 23(S) isomer. 0.63 (1.2H, s), 5.00 (2H, m), 0.65 (1.8H, s), 5.41 (1H, m), 1.01 (3H, s), 5.67 (1H, m), 1.05 (3H, m), 5.4–5.7 (1H, m), 2.04 (3H, s), 6.7–6.9 (1H, m), 2.09 (3H, s), (3) Preparation of compounds (13a) and (13b)

In 400 ml of acetone was dissolved 1216 mg of the above compound (12) (mixture of 23(R):23(S)=3:2), 5 ml of acetic acid was added thereto and the mixture was cooled to −40° C. Thereto was added 316 mg of potassium permanganate in a nitrogen atmosphere and the mixture was stirred at −40° C. to −37° C. for 2 hours. To the reaction mixture was added 20 ml of 1N HCl and the mixture was stirred for 20 minutes, followed by adding an aqueous sodium chloride solution and extraction with ethyl acetate. The organic layer was washed with water and concentrated and the residue was purified by silica gel column chromatography to obtain 359 mg of an isomer (13a) where the 23-position had S-configuration and 577 mg of an isomer (13b) where the 23-position had R-configuration.

NMR (CDCl$_3$, δ) of isomer (13a) 0.63 (3H, s), 1.01 (3H, s), 1.10 (3H, d, J=6.4 Hz), 2.04 (3H, s), 2.09 (3H, s), 5.0 (2H, m), 5.39 (1H, m), 5.68 (1H, m), 5.3–5.7 (1H, m)

NMR (CDCl$_3$, δ) of isomer (13b) 0.65 (3H, s), 1.01 (3H, s), 1.06 (3H, d, J=6.3 Hz), 2.04 (3H, s), 2.09 (3H, s), 5.0 (2H, m), 5.39 (1H, m), 5.3–5.65 (1H, m), 5.68 (1H, m)

(4) Preparation of compounds (14a) and (14b)

A mixture of tetrahydrofuran (10 ml), water (1 ml) and sodium borohydride (0.3 g) was cooled to 2° C. and thereto was added 300 mg of compound (13a). The reaction mixture was stirred at 0° to 5° C. for 30 minutes and then was extracted with addition of an aqueous sodium chloride solution and ethyl acetate. The organic layer was washed with water and concentrated to obtain a 13:7 mixture of compound (14a) and compound (14b). This mixture was subjected to silica gel column chromatography to obtain 186 mg (62% yield) of compound (14a) and 98 mg (33% yield) of compound (14b).

NMR (CDCl$_3$, δ) of isomer (14a) 0.63 (3H, s), 1.01 (3H, s), 1.03 (3H, d, J=6.6 Hz), 2.04 (3H, s), 2.09 (3H, s), 3.92 (1H, d-d, J=10 Hz, 23 Hz), 4.9–5.2 (3H, m), 5.39 (1H, m), 5.39 (1H, m), 5.68 (1H, m)

NMR (CDCl$_3$, δ) of isomer (14b) 0.63 (3H, s), 1.02 (3H, s), 1.07 (3H, d, J=6.6 Hz), 2.04 (3H, s), 2.09 (3H, s), 4.18 (1H, m), 4.9–5.2 (3H, m), 5.39 (1H, m), 5.68 (1H, m)

(5) Preparation of compound (16a)

In 10 ml of pyridine, 150 mg of the above compound (14a) was dissolved and thereto was added 0.2 ml of methanesulfonyl chloride. This was left to stand at room temperature for 3 hours. To the reaction mixture was added 1 ml of water and the mixture was stirred for 20 minutes and then extracted with addition of water and benzene. The organic layer was washed successively with 1N HCl and water and concentrated under reduced pressure to obtain compound (15a). To this compound (15a) was added 10 ml of triethylamine and the mixture was stirred at room temperature for 30 minutes and concentrated under reduced pressure. The residue was purified by silica gel column chromatography to obtain 128 mg (88% yield) of compound (16a).

(6) Preparation of compound (17a)

In 2 ml of tetrahydrofuran (THF), 60 mg of compound (16a) was dissolved and thereto was added 0.5 ml of 1M tetra-n-butylammonium fluoride-THF solution. The mixture was allowed to stand at room temperature for 30 minutes. To the reaction mixture was added ethyl acetate and the mixture was washed successively with 1N HCl and water and then concentrated under reduced pressure to obtain 50 mg (95% yield) of compound (17a).

NMR (CDCl$_3$, δ) 0.64 (3H, s), 1.01 (3H, s), 1.04 (3H, d, J=6.6 Hz), 2.04 (3H, s), 2.09 (3H, s), 4.76 (1H, d-d, J=25 Hz, 43 Hz), 4.9–5.3 (3H, m), 5.40 (1H, m), 5.60 (1H, m)

(7) Preparation of compound (20a)

Into a solution prepared by dissolving 20 mg of compound (17a) in 200 ml of benzene and 100 ml of n-hexane was introduced nitrogen gas at 0° C. to 5° C. for 15 minutes. The solution was irradiated by a 100 W high pressure mercury lamp. The reaction mixture was concentrated under reduced pressure at 20° C. or lower and the residue was subjected to silica gel column chromatography to obtain 7 mg of fraction mainly composed of compound (18a) and 13 mg of fraction mainly composed of the starting compound (17a). To 7 mg of the fraction of compound (18a) was added 20 ml of ethyl acetate and the mixture was refluxed for 3 hours in a nitrogen atmosphere and then concentrated under reduced pressure to obtain a crude compound (19a). This product was dissolved in a 5% NaOH-methanol solution and left to stand at 0° C. to 2° C. for 18 hours. Then, the solution was acidified with 1N HCl and extracted with ethyl acetate. The organic layer was washed with water and concentrated under reduced pressure. The residue was subjected to silica gel column chromatography and eluted with ethyl acetate-n-hexane (1:1) to obtain 2.8 mg of compound (20a).

UV spectrum (EtOH, nm): λmax 264.5 λmin 228

NMR (CDCl$_3$, δ) 0.58 (3H, s), 1.03 (3H, d, J=6.3 Hz), 4.22 (1H, m), 4.45 (1H, m), 4.76 (1H, d-d, J=25 Hz, 43 Hz), 5.04 (1H, s), 4.9–5.2 (1H, m), 5.33 (1H, s), 6.02 (1H, d, J=11 Hz), 6.38 (1H, d, J=11 Hz)

Example 4

Preparation of 23(S), 24(S)-23,26,26,26,27,27,27-heptafluoro-1α,24,25-trihydroxyvitamin D$_3$ (compound 21a)

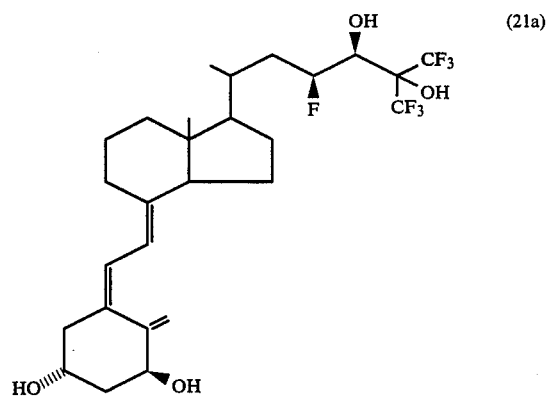

By substantially the same method as in the preparation of compound (20a) from compound (17a) in Example 3, 1.8 mg of compound (21a) was obtained from 20 mg of compound (14a) by subjecting compound (14a) to irradiation with ultraviolet light, thermal isomerization and then hydrolysis.

UV spectrum (EtOH, nm): λmax 264 λmin 227.5

NMR (CDCl$_3$, δ) 0.57 (3H, s), 4.9–5.2 (1H, m), 1.04 (3H, d, J=6.4 Hz), 5.33 (1H, s), 4.21 (1H, m), 6.02 (1H, d, J=11 Hz), 4.44 (1H, m), 6.38 (1H, d, J=11 Hz), 5.00 (1H, s)

Example 5

Preparation of 23(S)-1α,25-dihydroxy-23,26,26,26,27,27,27-heptafluorovitamin D$_3$ (compound 23a)

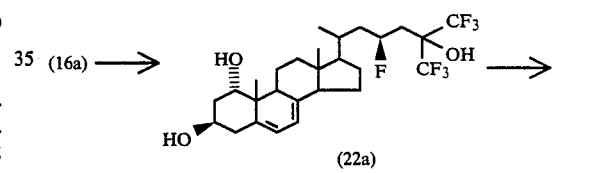

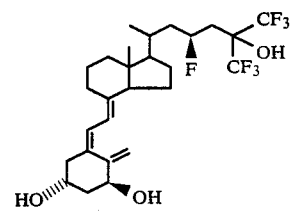

(1) Preparation of compound (22a)

In 10 ml of tetrahydrofuran, was dissolved 20 mg of compound (16a) obtained in Example 3 and cooled to 0° C. to 5° C., followed by adding 0.1 g of lithium aluminum hydride. The reaction mixture was stirred at the same temperature for 30 minutes, followed by adding water and extracting with ethyl acetate. The organic layer was washed with water and concentrated to obtain 15 mg (91% yield) of compound (22a).

NMR (CDCl$_3$, δ) 0.65 (3H, s), 1.01 (3H, d, J=6 Hz), 3.76 (1H, b-s), 4.03 (1H, m), 5.0–5.3 (1H, m), 5.38 (1H, m), 5.72 (1H, m)

(2) Preparation of compound (23a)

In a mixture of 20 ml of benzene and 100 ml of n-hexane, 15 mg of compound (22a) was dissolved and the solution was cooled to 0° C. to 5° C. The reaction mixture was irradiated by a 100 W high pressure mercury lamp for 3 minutes while introducing a nitrogen gas thereinto and then was concentrated under reduced pressure. The residue was dissolved in 10 ml of ethyl acetate and the solution was refluxed for 3 hours and then concentrated under reduced pressure to obtain a crude compound (23a). This was subjected to HPLC (column: Zorbax BP-SIL®, 8 mm∅×25 cm; carrier: ethyl acetate-n-hexane 3:2; flow rate: 1.5 ml/min) and the fraction of a retention time of 23 minutes was collected to obtain 2.5 mg (17% yield) of compound (23a).

UV spectrum (EtOH, nm): λmax 264.5, λmin 228

NMR (CDCl$_3$, δ) 0.57 (3H, s), 1.01 (3H, d, J=6.3 Hz), 4.23 (1H, b-s), 4.43 (1H, m), 5.00 (1H, s), 5.0–5.3 (1H, m), 5.33 (1H, s), 6.02 (1H, d, J=11.0 Hz), 6.38 (1H, d, J=11.0 Hz)

Example 6

Preparation of 23(R)-1α,25-dihydroxy-23,26,26,26,27,27,27-heptafluorovitamin D$_3$ (compound 23b)

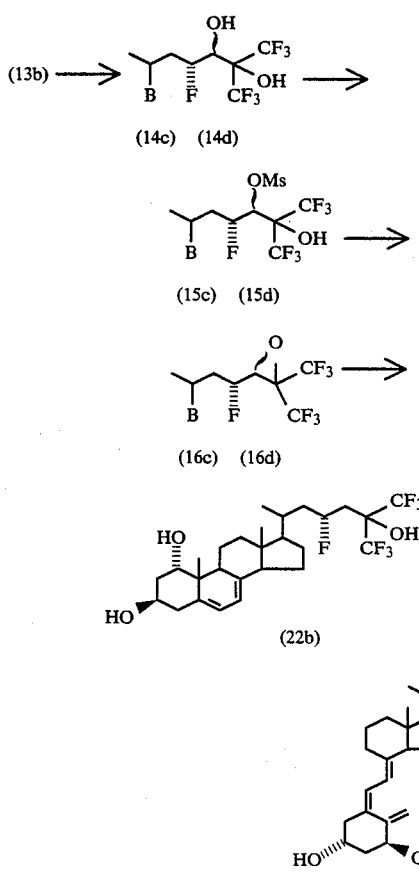

(1) Preparation of compounds (14c) and (14d)

In the same manner as in preparation of compounds (14a) and (14b) of Example 3, 300 mg of compound (13b) obtained in Example 3 where the 23-position had R-configuration was reduced with sodium borohydride to obtain 300 mg (99% yield) of a 7:3 mixture of compound (14c) where the 24-position had S-configuration and compound (14d) where the 24-position had R-configuration. This product was used, as it was, for the following step without separating the compounds (14c) and (14d).

NMR (CDCl$_3$, δ) of a mixture of compounds (14c) and (14d) 0.64 (3H, s), 1.01 (3H, s), 1.06 (3H, m), 2.04 (3H, s), 2.09 (3H, s), 3.84 (0.7H, d, J=22 Hz), 3.19 (0.3H, m), 4.75–5.2 (3H, m), 5.39 (1H, m), 5.69 (1H, m)

(2) Preparation of compounds (16c) and (16d)

In the same manner as in preparation of compound (16a) of Example 3, 200 mg of the mixture of compounds (14c) and (14d) was treated to obtain 165 mg (85% yield) of a mixture of two kinds of isomers (16c) and (16d) different in configuration at the 24-position.

NMR (CDCl$_3$, δ) 0.65 (3H, s), 3.5–3.7 (1H, m), 0.98 (3H, d, J=6 Hz), 4.5–4.85 (1H, m), 1.02 (3H, s), 5.0 (2H, m), 2.04 (3H, s), 5.39 (1H, m), 2.09 (3H, s), 5.69 (1H, m)

(3) Preparation of compound (22b)

In the same manner as in preparation of compound (22a) of Example 5, 30 mg of the mixture of compounds (16c) and (16d) was treated to obtain 25 mg (94% yield) of compound (22b).

NMR (CDCl$_3$—CD$_3$OD, δ) 0.65 (3H, s), 0.93 (3H, s), 1.03 (3H, d, J=6.3 Hz), 3.74 (1H, b-s), 4.0 (1H, m), 4.9–5.3 (1H, m), 5.35 (1H, m), 5.70 (1H, m) (4) Preparation of compound (23b)

In the same manner as in preparation of compound (23b) of Example 5, 20 mg of compound (22b) was subjected to reaction and finally the reaction product was subjected to the same HPLC as in Example 5 to obtain 3.8 mg (19% yield) of compound (23b).

UV spectrum (EtOH, nm): λmax 265 nm, λmin 227 nm

NMR (CDCl$_3$, δ) 0.58 (3H, s), 1.00 (3H, d, J=6.6 Hz), 4.23 (1H, b-s), 4.43 (1H, m), 5.00 (1H, s), 5.0–5.3 (1H, m), 5.32 (1H, s), 6.02 (1H, d, J=11.8 Hz), 6.38 (1H, d, J=11.5 Hz)

This product showed a retention time of 22 minutes in HPLC of the same conditions as in preparation of compound (23a).

What is claimed is:

1. A compound represented by the general formula:

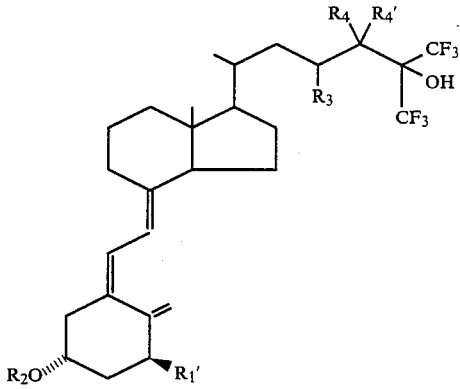

wherein R$_1$' denotes a hydrogen atom, a hydroxyl group or a protected hydroxyl group, R$_2$ denotes a hydrogen atom or a protecting group for hydroxyl group, R$_3$ denotes a fluorine atom, a hydroxyl group or a protected hydroxyl group and R$_4$ and R$_4$' each denotes a hydrogen atom, or one of them denotes a hydrogen atom and the other denotes a fluorine atom, hydroxyl group or a protected hydroxyl group or R$_4$ and R$_4$' are combined to denote an oxo group, with a proviso that at least one of R$_3$, R$_4$ and R$_4$' denotes a fluorine atom.

2. A compound of claim 1 wherein R$_1$' is a hydroxyl group or a protected hydroxyl group.

3. A compound represented by the general formula:

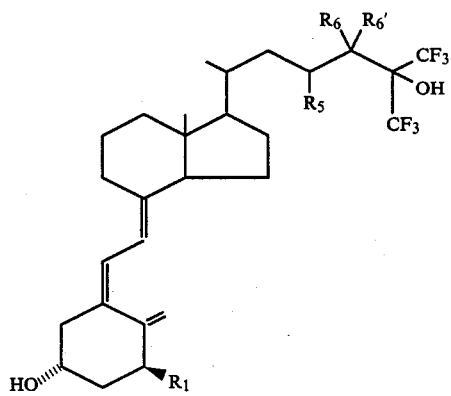

wherein $R_1$ denotes a hydrogen atom or a hydroxyl group, $R_5$ denotes a fluorine atom or a hydroxyl group and $R_6$ and $R_6'$ each denotes a hydrogen atom, or one of them denotes hydrogen atom and the other denotes a fluorine atom or a hydroxyl group or $R_6$ and $R_6'$ together denote an oxo group, with a proviso that at least one of $R_5$, $R_6$ and $R_6'$ denotes a fluorine atom.

4. A compound of claim 3 wherein $R_1$ is a hydroxyl group.

5. A compound of claim 4 wherein $R_5$ is a fluorine atom.

6. A compound of claim 4 wherein one of $R_6$ and $R_6'$ is a fluorine atom and the other is a hydrogen atom.

7. A compound of claim 3 which is 1α,25-dihydroxy-23,26,26,26,27,27,27-heptafluorovitamin $D_3$.

8. A compound of claim 3 which is 1α,25-dihydroxy-23,24,26,26,26,27,27,27-octafluorovitamin $D_3$.

9. A compound of claim 3 which is 23,26,26,26,27,27,27-heptafluoro-1α,24,25-trihydroxy-vitamin $D_3$.

10. A compound of claim 3 which is 24,26,26,26,27,27,27-heptafluoro-1α,23,25-trihydroxy-vitamin $D_3$.

11. A compound of claim 3 which is 1α,25-dihydroxy-23,26,26,26,27,27,27-heptafluoro-24-oxovitamin $D_3$.

12. A pharmaceutical composition useful as a curative agent for diseases caused by disorders of absorption, transportation or metabolism of calcium, cell-differentiation, rheumatism or psoriasis which comprises as an active ingredient a pharmacologically effective amount of a compound of claim 3 and a pharmacologically acceptable carrier.

13. A method of inducing cell differentiation which comprises administering a pharmaceutically effective amount of a compound of claim 3 to a patient in need of such treatment.

14. A method of treating diseases caused by disorders of absorption, transporation or metabolism of calcium, rheumatism or psoriasis which comprises administering a pharmaceutically effective amount of a compound of claim 3 to a patient in need of such treatment.

15. A process for preparing a vitamin $D_3$ derivative represented by the general formula:

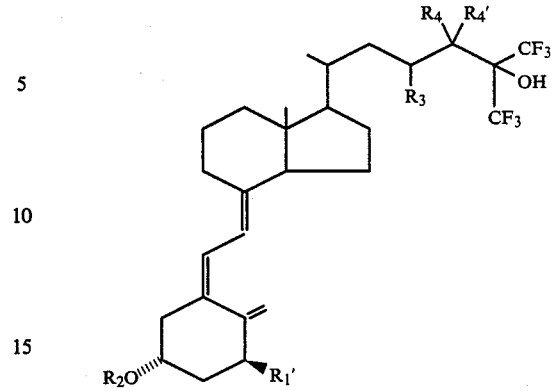

wherein $R_1'$ denotes a hydrogen atom a hydroxyl group or a protected hydroxyl group. $R_2$ denotes a hydrogen atom or a protecting group for hydroxyl group, $R_3$ denotes a fluorine atom, a hydroxyl group or a protected hydroxyl group and $R_4$ and $R_4'$ which denotes a hydrogen atom or one of them denotes a hydrogen atom and the other denotes a fluorine atom, hydroxyl group or a protected hydroxyl group or $R_4$ and $R_4'$ are combined to denote an oxo group, with a proviso that at least one of $R_3$, $R_4$ and $R_4'$ denotes a fluorine atom which comprises subjecting a compound represented by the general formula:

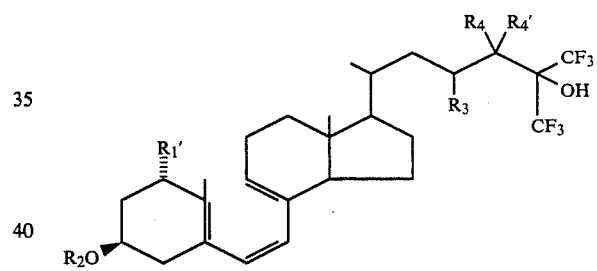

wherein $R_1'$, $R_2$, $R_3$, $R_4$ and $R_4'$ are the same as defined above, to thermal isomerization and optionally further to deprotection reaction.

16. A compound represented by the general formula:

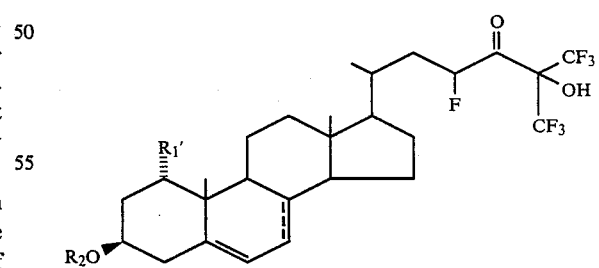

wherein $R_1'$ denotes a hydrogen atom, a hydroxyl group or a protected hydroxyl group, $R_2$ denotes a hydrogen atom or a protecting group for hydroxyl group and the dotted line . . . between the carbon atoms of the 7- and 8-position signifies the optional presence of a bond.

17. A process for producing a compound represented by the general formula:

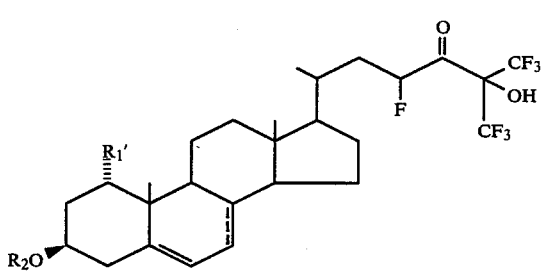

wherein $R_1'$ denotes a hydrogen atom a hydroxyl group or a protected hydroxyl group, $R_2$ denotes a hydrogen atom or a protecting group for hydroxyl group and the dotted line . . . between the carbon atoms of the 7- and 8-position signifies the optional presence of a bond which comprises reacting a compound represented by the general formula:

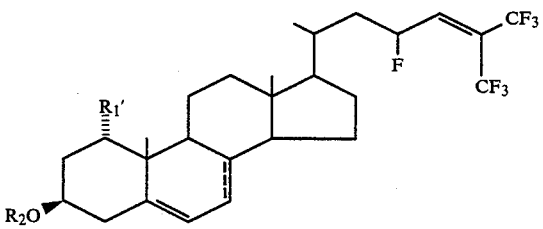

wherein $R_1'$, $R_2$ and the dotted line are the same as defined above, with a permanganate in the presence of an acid.

18. A compound represented by the general formula:

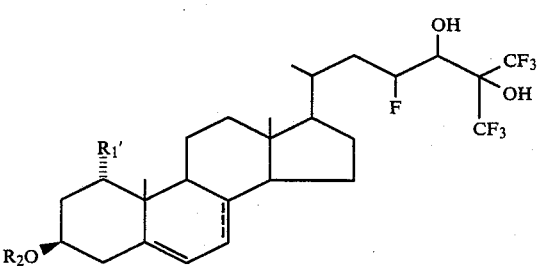

wherein $R_1'$ denotes a hydrogen atom, a hydroxyl group or a protected hydroxyl group, $R_2$ denotes a hydrogen atom or a protecting group for hydroxyl group and the dotted line . . . between the carbon atoms of the 7- and 8-positions signifies the optional presence of a double bond.

19. A process for producing a compound represented by the general formula:

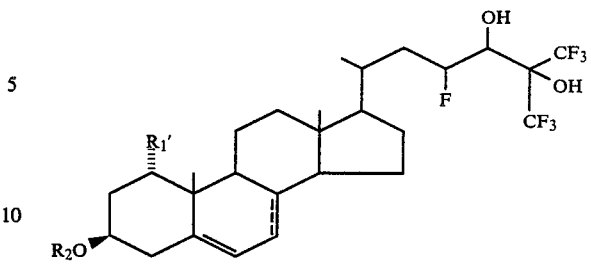

wherein $R_1'$ denotes a hydrogen atom, a hydroxyl group or a protected hydroxyl group, $R_2$ denotes a hydrogen atom or a protecting group for hydroxyl group and the dotted line . . . between the carbon atoms of the 7- and 8-positions signifies the optional presence of a double bond which comprises reacting a compound represented by the general formula:

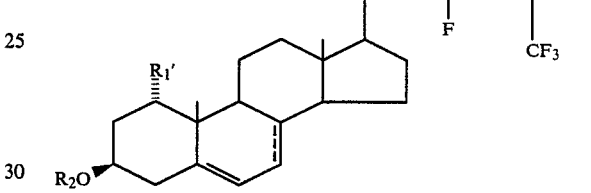

wherein $R_1'$, $R_2$ and the dotted line are the same as defined above, with a permanganate in the presence of a base.

20. A compound represented by the general formula:

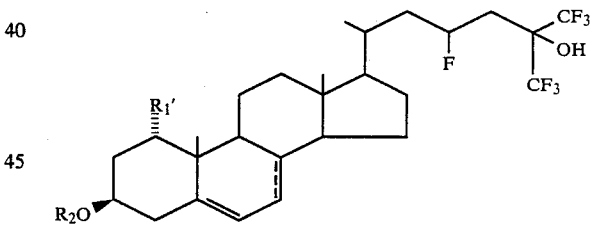

wherein $R_1'$ denotes a hydrogen atom, a hydroxyl group or a protected hydroxyl group, $R_2$ denotes a hydrogen atom or a protecting group for hydroxyl group and the dotted line . . . between the carbon atoms of the 7- and 8-positions signifies the optional presence of a bond.

21. A process for producing a compound represented by the general formula:

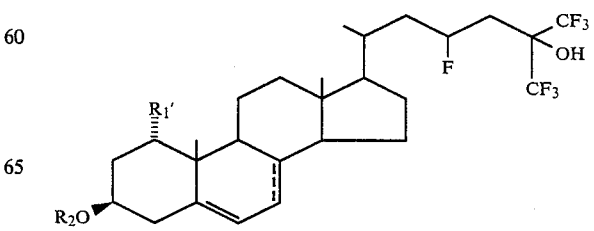

wherein $R_1'$ denotes a hydrogen atom a hydroxyl group or a protected hydroxyl group, $R_2$ denotes a hydrogen atom or a protecting group for hydroxyl group and the dotted line ... between the carbon atoms of the 7- and 8-positions signifies the optional presence of a bond which comprises reducing with a reducing agent a compound represented by the general formula:

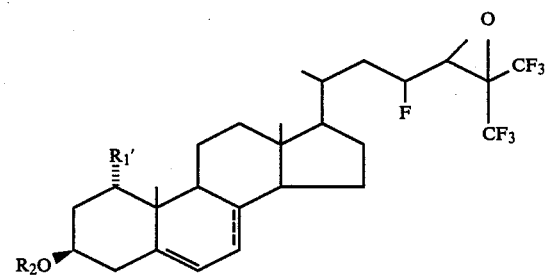

wherein $R_1'$, $R_2$ and the dotted line are the same as above.

22. A compound represented by the general formula:

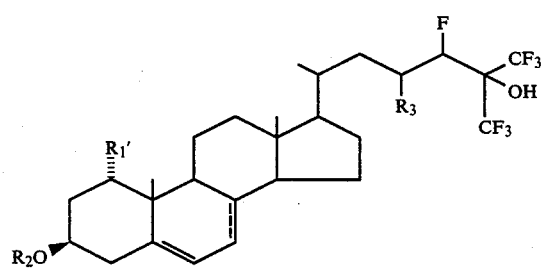

wherein $R_1'$ denotes a hydrogen atom, a hydroxyl group or a protected hydroxyl group, $R_2$ denotes a hydrogen atom or a protecting group for hydroxyl group, $R_3$ denotes a hydrogen atom, a fluorine atom, a hydroxyl group or a protected hydroxyl group and the dotted line between the carbon atoms of the 7- and 8-positions signifies the optional presence of a bond.

23. A process for producing a compound represented by the general formula:

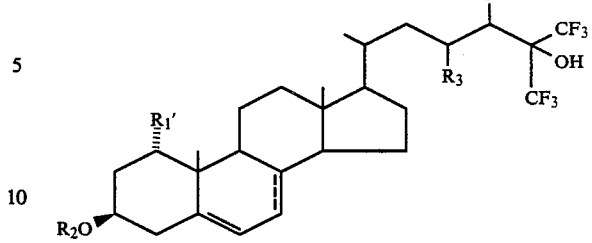

wherein $R_1'$ denotes a hydrogen atom a hydroxyl group or a protected hydroxyl group, $R_2$ denotes a hydrogen atom or a protecting group for hydroxyl group, $R_3$ denotes a hydrogen atom a fluorine atom, a hydroxyl group or a protected hydroxyl group and the dotted line between the carbon atoms of the 7-and 8-positions signifies the optional presence of a bond which comprises reacting a compound represented by the general formula:

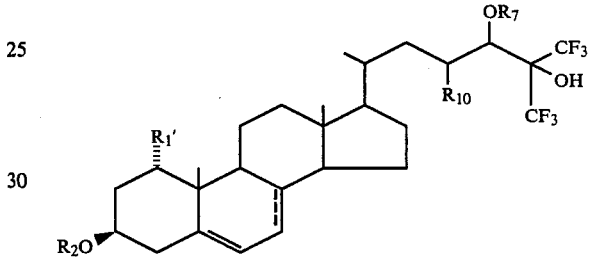

wherein $R_1'$, $R_2$ and the dotted lines are the same as defined above $R_7$ denotes an alkansulfonyl group or an arenesulfonyl group and $R_{10}$ denotes a hydrogen atom, a fluorine atom or a protected hydroxyl group or a compound represented by the general formula:

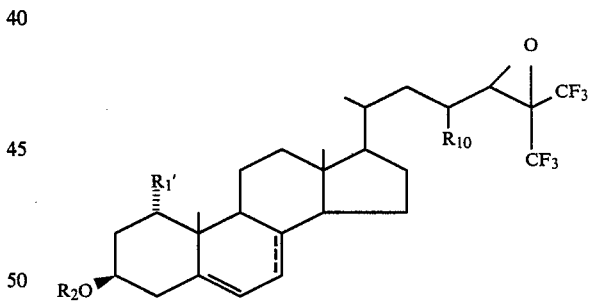

wherein $R_1'$, $R_2$ and the dotted line and $R_{10}$ are the same as defined above, with a fluorinating agent and optionally subjecting the reaction product to deprotection reaction.

* * * * *

UNITED STATES PATENT AND TRADEMARK OFFICE
CERTIFICATE OF CORRECTION

PATENT NO.   :   4,853,378

DATED        :   AUGUST 1, 1989

INVENTOR(S)  :   Noritaka HAMMA et al

It is certified that error appears in the above-identified patent and that said Letters Patent is hereby corrected as shown below:

IN THE HEADING OF THE PATENT,

Correct Item "[73]" to read as follows:

-- [73] Assignee:  Sumitomo Pharmaceuticals Company, Limited, Osaka, Japan --

Signed and Sealed this

Seventeenth Day of September, 1991

Attest:

HARRY F. MANBECK, JR.

*Attesting Officer*      *Commissioner of Patents and Trademarks*